United States Patent
Lee et al.

(10) Patent No.: US 11,921,273 B2
(45) Date of Patent: Mar. 5, 2024

(54) TWO-PHOTON EXCITED FLUORESCENCE MICROSCOPE FOR DIAGNOSIS OF ALZHEIMER'S DISEASE (AD) AND MILD COGNITIVE IMPAIRMENT (MCI), AND PULSE COMPRESSOR INCLUDING THEREIN

(71) Applicant: Electronics and Telecommunications Research Institute, Daejeon (KR)

(72) Inventors: Sang Kyun Lee, Daejeon (KR); Dong Hoon Song, Daejeon (KR); Hong-Seok Seo, Daejeon (KR); Chul Huh, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 248 days.

(21) Appl. No.: 17/460,478

(22) Filed: Aug. 30, 2021

(65) Prior Publication Data
US 2022/0137387 A1    May 5, 2022

(30) Foreign Application Priority Data

Oct. 30, 2020  (KR) .......................... 10-2020-0143007
Jul. 22, 2021  (KR) .......................... 10-2021-0096508

(51) Int. Cl.
*G02B 21/00*    (2006.01)
*A61B 5/00*    (2006.01)
(Continued)

(52) U.S. Cl.
CPC ........ *G02B 21/0076* (2013.01); *A61B 5/4088* (2013.01); *G02B 21/361* (2013.01); *H01S 3/0057* (2013.01)

(58) Field of Classification Search
CPC .. G02B 21/0076; G02B 21/361; G02B 21/00; G02B 21/0004; G02B 21/002; G02B 21/0024; G02B 21/0032; G02B 21/0052; G02B 21/0064; G02B 21/0072; G02B 21/06; G02B 21/36; G02B 5/12; G02B 5/122; G02B 5/18; G02B 2005/1804;
(Continued)

(56) References Cited

U.S. PATENT DOCUMENTS 5,812,567 A      9/1998  Jeon et al.
5,995,281 A  *  11/1999  Simon .................. G02B 21/002
                                                              359/368
(Continued)

FOREIGN PATENT DOCUMENTS

CN     209561848 U    10/2019
CN     111537477 A     8/2020
(Continued)

*Primary Examiner* — Arnel C Lavarias
(74) *Attorney, Agent, or Firm* — NSIP Law

(57) ABSTRACT

Provided are a pulse compressor and a two-photon excited fluorescence microscope. The microscope includes a light source which generates a laser beam having a pulse, a pulse compressor which compresses the pulse of the laser beam, an objective lens which provides the laser beam to a specimen, and image sensors which receive the laser beam and obtain images of the specimen. The pulse compressor may include a grating plate, a corner cube provided on one side of the grating plate, and a retroreflector provided on the other side of the grating plate.

16 Claims, 5 Drawing Sheets

(51) Int. Cl.
*G02B 21/36* (2006.01)
*H01S 3/00* (2006.01)

(58) Field of Classification Search
CPC .. G02B 5/1814; G02B 5/1819; G02B 5/1828; G02B 5/1866; G02B 27/42; G02B 27/4233; G02B 27/4244; G02B 27/425; G02B 27/0025; G02B 27/0037; G02B 27/0068; A61B 5/4088; H01S 3/0057
USPC ....... 359/381, 362, 363, 368, 369, 384, 385, 359/388, 390, 558, 566, 569, 573, 574, 359/529
See application file for complete search history.

(56) References Cited

U.S. PATENT DOCUMENTS

| | | | | |
|---|---|---|---|---|
| 6,449,039 | B1 * | 9/2002 | Bouzid | G02B 21/06 |
| | | | | 356/318 |
| 10,040,146 | B2 * | 8/2018 | Squier | G01B 11/00 |
| 10,862,263 | B1 * | 12/2020 | Al-Kadry | H01S 3/094076 |
| 2007/0076199 | A1 | 4/2007 | Ode | |
| 2008/0151238 | A1 | 6/2008 | Zhu et al. | |
| 2015/0214688 | A1 | 7/2015 | Song et al. | |
| 2017/0370834 | A1 | 12/2017 | Kassab et al. | |
| 2020/0319445 | A1 | 10/2020 | Schumann et al. | |
| 2023/0253750 | A1 * | 8/2023 | Budnicki | H01S 3/0057 |
| | | | | 372/25 |

FOREIGN PATENT DOCUMENTS

| | | | | |
|---|---|---|---|---|
| JP | 2007-65149 | A | 3/2007 | |
| JP | 2017-135315 | A | 8/2017 | |
| JP | 2018-72735 | A | 5/2018 | |
| JP | 2019-517027 | A | 6/2019 | |
| KR | 10-2014-0049826 | A | 4/2014 | |
| KR | 10-2017-0110496 | A | 10/2017 | |
| KR | 10-2020-0028824 | A | 3/2020 | |
| WO | WO-2019201791 | A1 * | 10/2019 | G02B 5/122 |

* cited by examiner

TWO-PHOTON EXCITED FLUORESCENCE MICROSCOPE FOR DIAGNOSIS OF ALZHEIMER'S DISEASE (AD) AND MILD COGNITIVE IMPAIRMENT (MCI), AND PULSE COMPRESSOR INCLUDING THEREIN

CROSS-REFERENCE TO RELATED APPLICATIONS

This U.S. non-provisional patent application claims priority under 35 U.S.C. § 119 of Korean Patent Application Nos. 10-2020-0143007, filed on Oct. 30, 2020, and 10-2021-0096508, filed on Jul. 22, 2021, the entire contents of which are hereby incorporated by reference.

BACKGROUND

The present disclosure herein relates to a microscope, and more particularly, to a two-photon excited fluorescence microscope for diagnosis of Alzheimer's disease, mild cognitive impairment (MCI), and a pulse compressor included therein.

Early diagnosis is very important for progressive neurodegenerative diseases such as Alzheimer's disease. Generally, diagnosis of Alzheimer's disease has been performed mainly by a magnetic resonance imaging (MRI) apparatus. However, the MRI apparatus can diagnose Alzheimer's disease with brain damage, but cannot diagnose Alzheimer's disease early. Thus, there is a need for the development of a diagnosis device for Alzheimer's disease at an early stage.

SUMMARY

The present disclosure provides a two-photon excited fluorescence microscope capable of diagnosing mild cognitive impairment (MCI) or Alzheimer's disease.

The present disclosure also provides a pulse compressor which may be reduced in size and have a wavelength changing function and a high-order dispersion correction function.

Disclosed is a two-photon excited fluorescence microscope. An embodiment of the inventive concept provides a two-photon excited fluorescence microscope including: a light source configured to generate a laser beam having a pulse; a pulse compressor configured to compress a pulse of the laser beam and change a wavelength of the pulse; an objective lens configured to provide the laser beam to a specimen; and image sensors configured to receive the laser beam and obtain images of the specimen. Here, the pulse compressor may include: a grating plate configured to disperse the laser beam; a corner cube provided on one side of the grating plate and configured to reflect the laser beam to the grating plate; and a retroreflector provided on the other side of the grating plate and configured to re-reflect the laser beam, which has been transmitted through the grating plate, to the corner cube and the grating plate.

In an embodiment, the grating plate may include: a first diffraction region; a second diffraction region spaced apart from the first diffraction region; a third diffraction region between the second diffraction region and the first diffraction region; and a fourth diffraction region between the third diffraction region and the first diffraction region.

In an embodiment, the retroreflector may be in contact with the second diffraction region and the third diffraction region and spaced apart from the first diffraction region and the fourth diffraction region.

In an embodiment, the pulse compressor may further include a rotator, which is connected to a side wall of the grating plate adjacent to the first diffraction region to rotate the grating plate.

In an embodiment, the pulse compressor may further include a cylinder, which is provided between the third diffraction region and the fourth diffraction region and adjusts a distance between the grating plate and the corner cube.

The rotator and the cylinder may simultaneously rotate all of the grating plate, the corner cube, and retroreflector to adjust a distance to the corner cube.

In an embodiment, the light source may include a femtosecond pulse laser.

In an embodiment, the two-photon excited fluorescence microscope may further include beam splitters provided between the pulse compressor and the objective lens.

In an embodiment, the beam splitters may include: a first beam splitter; and a second beam splitter between the first beam splitter and the objective lens.

In an embodiment, the two-photon excited fluorescence microscope may further include tube lenses between the pulse compressor and the first beam splitter.

In an embodiment, the two-photon excited fluorescence microscope may further include planar mirrors between the tube lenses and the pulse compressor.

In an embodiment of the inventive concept, a pulse compressor includes: a grating plate configured to disperse a laser beam; a corner cube provided on one side of the grating plate and configured to reflect the laser beam to the grating plate; a retroreflector provided on the other side of the grating plate and configured to re-reflect the laser beam, which has been transmitted through the grating plate, to the corner cube and the grating plate; and a rotator connected to one side wall of the grating plate, the rotator rotating the grating plate to adjust a dispersion value of the laser beam and changing a wavelength thereof.

In an embodiment, the grating plate may include: a first diffraction region adjacent to the rotator; a second diffraction region spaced apart from the first diffraction region; a third diffraction region between the second diffraction region and the first diffraction region; and a fourth diffraction region between the third diffraction region and the first diffraction region.

In an embodiment, the retroreflector may be in contact with the second diffraction region and the third diffraction region, the retroreflector spaced apart from the first diffraction region and the fourth diffraction region.

In an embodiment, the pulse compressor may further include a cylinder provided between the third diffraction region and the fourth diffraction region to adjust a distance between the grating plate and the corner cube.

In an embodiment, the pulse compressor may further include a spatial light modulator provided between the grating plate and the corner cube.

In an embodiment, the spatial light modulator may be provided adjacent to the fourth diffraction region.

BRIEF DESCRIPTION OF THE FIGURES

The accompanying drawings are included to provide a further understanding of the inventive concept, and are incorporated in and constitute a part of this specification. The drawings illustrate embodiments of the inventive concept and, together with the description, serve to explain principles of the inventive concept. In the drawings.

DETAILED DESCRIPTION

Figure 1:
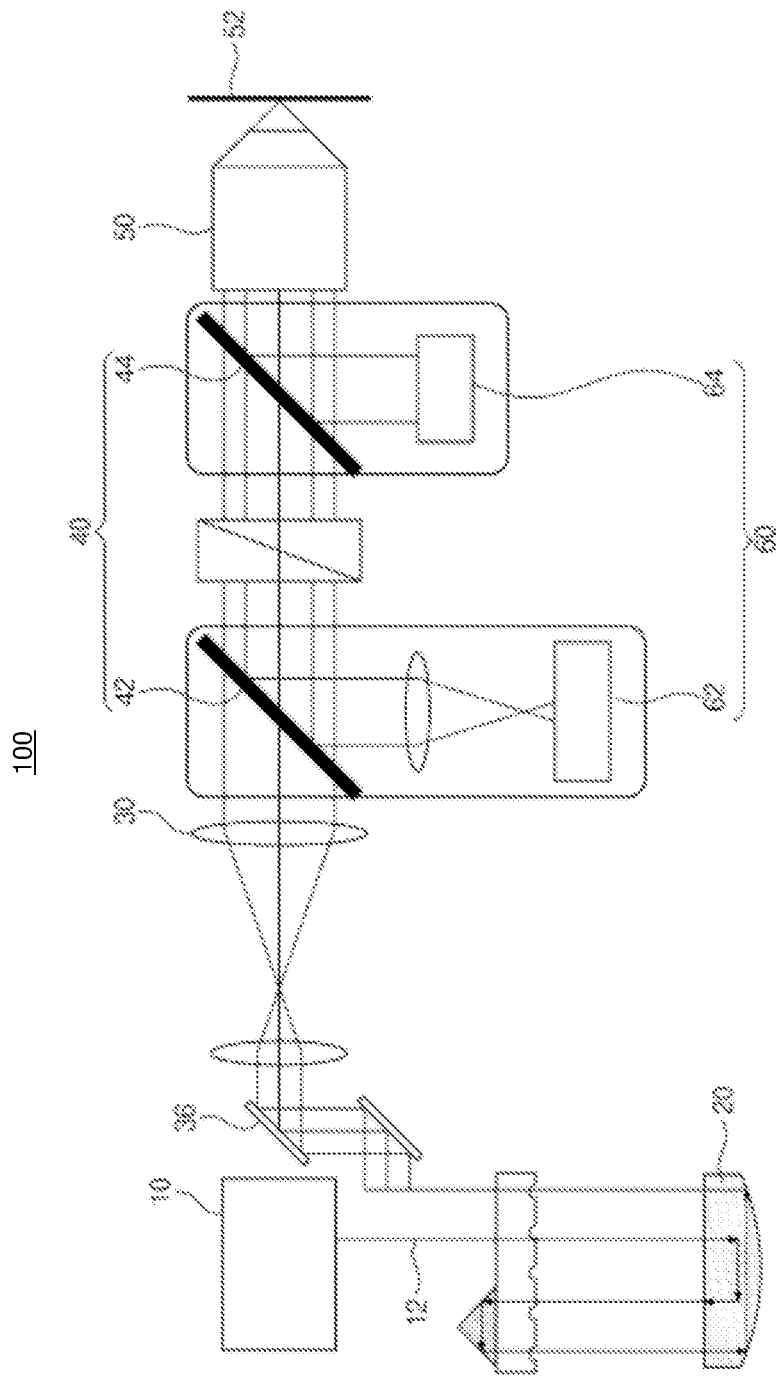
FIG. 1 is a cross-sectional view showing one example of a two-photon excited fluorescence microscope according to an embodiment of the inventive concept.

Hereinafter, embodiments of the inventive concept will be described in detail with reference to the accompanying drawings. Advantages and features of the present disclosure, and implementation methods thereof will be clarified through following embodiments described in detail with reference to the accompanying drawings. The present disclosure may, however, be embodied in different forms and should not be construed as limited to the embodiments set forth herein. Rather, these embodiments are provided so that this disclosure will be thorough and complete, and will fully convey the scope of the present disclosure to those skilled in the art. Further, the present disclosure is only defined by scopes of claims. Like reference numerals refer to like elements throughout.

The terms used in this specification are used only for explaining embodiments while not limiting the present disclosure. In this specification, the singular forms include the plural forms as well, unless the context clearly indicates otherwise. The meaning of 'comprises' and/or 'comprising' used in the specification does not exclude the presence or addition of one or more components, steps, operations, and/or elements other than the mentioned components, steps, operations, and/or devices. Also, in the specification, a femtosecond, two photons, and a microscope may be understood as having a meaning mainly used in the field of optics. Since preferred embodiments are provided below, the order of the reference numerals given in the description is not limited thereto.

FIG. 1 shows one example of a two-photon excited fluorescence microscope 100 according to an embodiment of the inventive concept.

Referring to FIG. 1, the two-photon excited fluorescence microscope 100 according to the embodiment of the inventive concept may include a light source 10, a pulse compressor 20, tube lenses 30, beam splitters 40, an objective lens 50, and image sensors 60.

The light source 10 may generate a laser beam 12. The laser beam 12 may have a femtosecond pulse. That is, the laser beam 12 may be a femtosecond pulse laser beam. For example, the light source 10 may include an about 75 femtosecond pulse Ti:sapphire laser device.

The pulse compressor 20 may be provided between the light source 10 and the tube lenses 30. The pulse compressor 20 may rotate about the light source 10 and adjust a dispersion value of the laser beam 12. That is, components of the pulse compressor 20 may have rotatable structures. For example, the pulse compressor 20 may adjust the dispersion value of the laser beam 12 to a negative value. On the other hand, the pulse compressor 20 may tune the wavelength of the laser beam 12. As one example, the pulse compressor 20 may be a grating plate pulse compressor.

Figure 2:
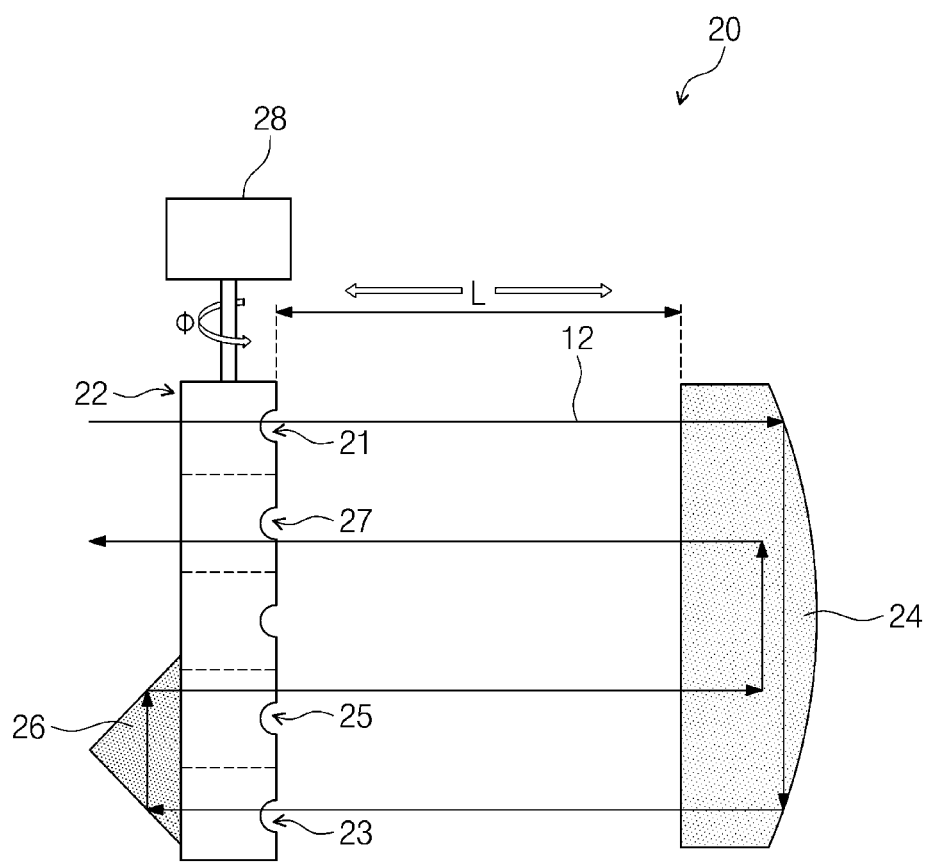
FIG. 2 is a cross-sectional view showing one example of a pulse compressor of FIG. 1.
Figure 3:
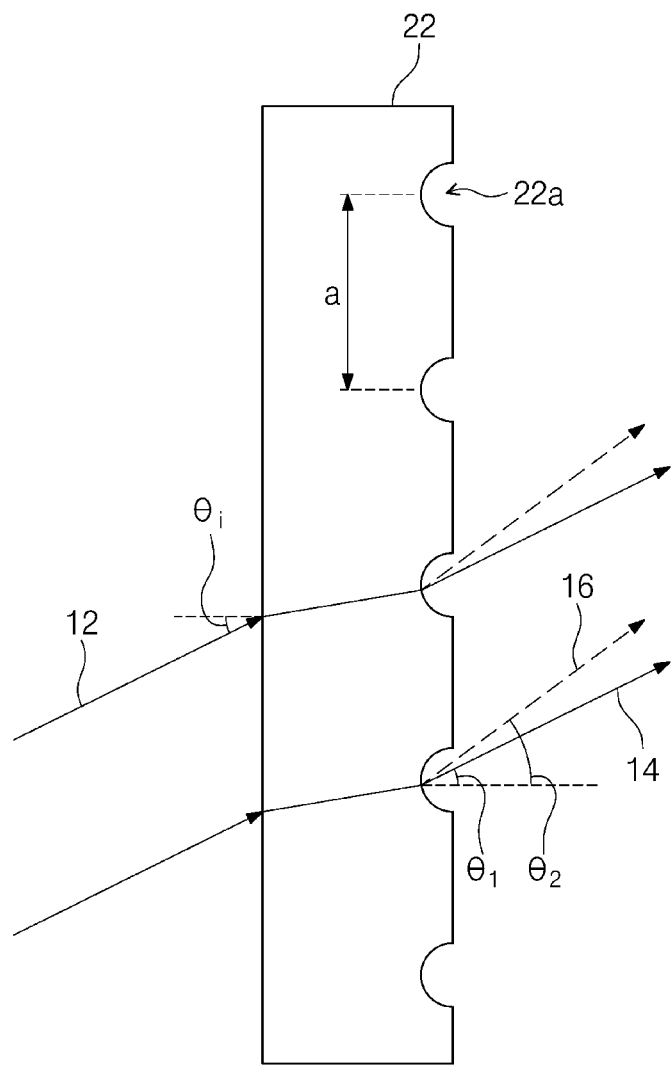
FIG. 3 is a cross-sectional view showing one example of a grating plate of FIG. 2.

FIG. 2 shows one example of the pulse compressor 20 of FIG. 1. FIG. 3 shows one example of a grating plate 22 of FIG. 2.

Referring to FIGS. 2 and 3, the pulse compressor 20 may include a grating plate 22, a corner cube 24, a retroreflector 26, and a rotator 28.

The grating plate 22 may be a visible transmission grating. The grating plate 22 may include a grating rod, but the embodiment of the inventive concept is not limited thereto. The grating plate 22 may allow the laser beam 12 to pass therethrough. Also, the grating plate 22 may diffract the laser beam 12. The grating plate 22 is provided between the corner cube 24 and the retroreflector 26 and may reduce the size of the pulse compressor 20. A chirped mirror and a reflection grating of a typical pulse compressor have a spaced distance of about 15 cm to about 30 cm, but the pulse compressor 20 including the grating plate 22 may have a significantly smaller size than the typical pulse compressor. For example, the pulse compressor 20 may have a size of about 5 cm$^3$ to about 10 cm$^3$. The grating plate 22 may have a correction range of a dispersion value wider than that of a prism of the typical pulse compressor.

Referring to FIG. 3, the grating plate 22 may have a plurality of gratings 22a. The gratings 22a may be provided on one side of the grating plate 22. The gratings 22a may have a distance of about 100 nm to about 100 μm. The gratings 22a may diffract the laser beam 12.

When the laser beam 12 has an incident angle $\theta_i$ and is provided on the other side of the grating plate 22, a first diffracted beam 14 and a second diffracted beam 16 may be generated. The first diffracted beam 14 may be a zero-order diffracted beam of the laser beam 12. For example, the first diffracted beam 14 may have a first diffraction angle $\theta_1$. The first diffraction angle $\theta_1$ may be equal to the incident angle $\theta_i$. The second diffracted beam 16 may be a first-order diffracted beam of the laser beam 12. The second diffracted beam 16 may have a second diffraction angle $\theta_2$. The second diffraction angle $\theta_2$ may be greater than the first diffraction angle $\theta_1$. Although not illustrated, the laser beam 12 may generate a third diffracted beam to an n-th diffracted beam through the grating plate 22. The dispersion value of the laser beam 12 may increase mainly in proportion to intensities of the second diffracted beam 16 to the n-th diffracted beam. The dispersion value of the laser beam 12 may be in proportion to a distance L between the grating plate 22 and the corner cube 24. The dispersion value of the laser beam 12 may be in proportion to a distance between the retroreflector 26 and the grating plate 22.

Also, the grating plate 22 may diffract the laser beam 12 four times through the reflection of the corner cube 24 and the retroreflector 26, and thus may reduce the dispersion value of the laser beam 12. The grating plate 22 may have about four diffraction regions for the laser beam 12. The dispersion value of the laser beam 12 may be reduced as the number of diffraction regions increases. For example, the grating plate 22 may have a first diffraction region 21, a second diffraction region 23, a third diffraction region 25, and a fourth diffraction region 27.

The first diffraction region 21 may be spaced apart from the retroreflector 26. The first diffraction region 21 may be a region that provides the laser beam 12 to the corner cube 24.

The second diffraction region 23 and the third diffraction region 25 may be regions which are in contact with the retroreflector 26. The second diffraction region 23 may be a region that provides the laser beam 12 from the corner cube 24 to the retroreflector 26.

The third diffraction region 25 may be provided between the first diffraction region 21 and the second diffraction region 23. The third diffraction region 25 may be a region that provides the laser beam 12 from the retroreflector 26 to the corner cube 24.

The fourth diffraction region 27 may be provided between the third diffraction region 25 and the first diffraction region 21. The fourth diffraction region 27 may be spaced apart from the retroreflector 26. The fourth diffraction region 27 may be a region that provides the laser beam 12 from the corner cube 24 to the grating plate 22.

As the laser beam 12 is provided to the first diffraction region 21, the second diffraction region 23, the third diffraction region 25, and the fourth diffraction region 27, the intensity of the second diffracted beam 16 may be sequentially reduced, and the dispersion value of the laser beam 12 may be reduced. Also, interference of the second diffracted beam 16 may increase. Thus, the dispersion value of the laser beam 12 may be reduced to a negative value.

The corner cube 24 may be provided on one side of the grating plate 22. When the laser beam 12 is provided from the grating plate 22, the corner cube 24 may internally reflect the laser beam 12 and provide the laser beam 12 to the grating plate 22. The corner cube 24 may have a flat surface and a rounded surface. The flat surface of corner cube 24 may allow the laser beam 12 to pass therethrough and provide the laser beam 12 to the rounded surface of corner cube 24. The rounded surface of corner cube 24 may reflect the laser beam 12 within the corner cube 24 and provide the laser beam 12 to the grating plate 22. The laser beam 12 may be reflected from the corner cube 24 to the grating plate 22. Although not illustrated, the corner cube 24 may include a reflection layer on the rounded surface.

The retroreflector 26 may be provided on the other side of the grating plate 22. The retroreflector 26 may be in contact with the second diffraction region 23 and the third diffraction region 25 of the grating plate 22. When the laser beam 12 is provided to the second diffraction region 23, the retroreflector 26 may reflect the laser beam 12 and provide the laser beam 12 to the third diffraction region 25. Thus, the corner cube 24 and the retroreflector 26 repeatedly reflect the laser beam 12 to the grating plate 22, and may reduce the size of the pulse compressor 20. The retroreflector 26 may have a triangular shape. Although not illustrated, the retroreflector 26 and the grating plate 22 may be coupled to each other by an adhesive. The adhesive may have the same refractive index as the retroreflector 26 and the grating plate 22.

A rotator 28 may be connected to a side wall of the grating plate 22 adjacent to the first diffraction region 21. The rotator 28 rotates the grating plate 22 in a direction of an azimuth angle $\phi$, and may minimize the dispersion value of the laser beam 12. Also, the rotator 28 rotates the grating plate 22 and may tune the wavelength of the laser beam 12.

Referring to FIG. 1 again, planar mirrors 36 may be provided between the pulse compressor 20 and the tube lenses 30. The planar mirrors 36 may change the path of the laser beam 12.

The tube lenses 30 may be provided between the planar mirrors 36 and the beam splitters 40. The tube lenses 30 may collimate the laser beam 12 into the beam splitters 40. The tube lenses 30 may magnify the size of the laser beam 12, but the embodiment of the inventive concept is not limited thereto.

The beam splitters 40 may be provided between the tube lenses 30 and the objective lens 50. The laser beam 12 of the light source 10 may be transmitted through the beam splitters 40, but the laser beam 12 of the objective lens 50 may be reflected from the beam splitters 40 to the image sensors 60. The beam splitters 40 may include dichroic mirrors. The beam splitters 40 may include a first beam splitter 42 and a second beam splitter 44. The first beam splitter 42 may be provided between the tube lenses 30 and the second beam splitter 44. The second beam splitter 44 may be provided between the first beam splitter 42 and the objective lens 50.

The objective lens 50 may focus the laser beam 12 on a specimen 52. The laser beam 12 may be transmitted through a portion of the specimen 52. The specimen 52 may reflect a portion of the laser beam 12. The specimen 52 may include the eyeball of the human body. The laser beam 12 may be provided to the fundus or retina within the eyeball of the human body. The objective lens 50 may receive the laser beam 12 reflected from the specimen 52. For example, the objective lens 50 may include Olympus XLUMPlanF1 20X/NA 0.95 dipping objective lens.

The image sensors 60 may be disposed adjacent to the beam splitters 40. The image sensors 60 may receive the laser beam 12 and obtain images of the specimen 52. For example, the image sensors 60 may include a CMOS sensor or a CCD sensor. As one example, the image sensors 60 may include a first image sensor 62 and a second image sensor 64. The first image sensor 62 may be provided adjacent to the first beam splitter 42. The first image sensor 62 may obtain images of the surface of the specimen 52. The first image sensor 62 may obtain an image of the eyeball.

The second image sensor 64 may be provided adjacent to the second beam splitter 44. The second image sensor 64 may obtain images inside the specimen 52. The second image sensor 64 may obtain an image of the fundus.

The control unit (not shown) may allow the images of the surface of the specimen 52 by the first image sensor 62 to be displayed on a display device (not shown). Also, the control unit may allow the images inside the specimen 52 by the second image sensor 64 to be displayed on the display device. In particular, the control unit may use the image of the fundus of the second image sensor 64 to diagnose the dementia and the mild cognitive impairment of the specimen 52.

Thus, the two-photon excited fluorescence microscope 100 according to the embodiment of the inventive concept transmits a portion of the laser beam 12, of which the dispersion value has been adjusted to a negative value, into the specimen 52, and obtains the images of the fundus, thereby diagnosing the dementia or the mild cognitive impairment which is a previous stage of dementia.

Figure 4:
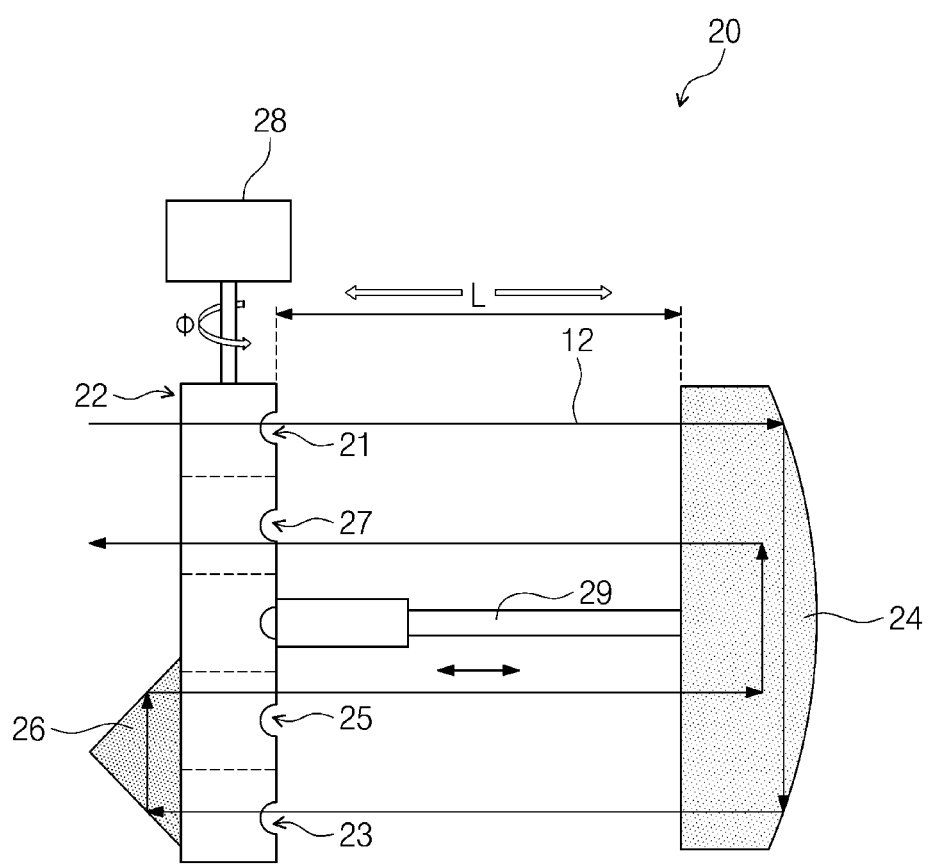
FIG. 4 is a cross-sectional view showing one example of a pulse compressor of FIG. 1.

FIG. 4 shows one example of the pulse compressor 20 of FIG. 1.

Referring to FIG. 4, the pulse compressor 20 may further include a cylinder 29. The cylinder 29 may be provided between a third diffraction region 25 and a fourth diffraction region 27 of a grating plate 22. The cylinder 29 may adjust a distance L between the grating plate 22 and a corner cube 24 to reduce the dispersion value of the laser beam 12, thereby changing the wavelength of the laser beam 12.

Figure 5:
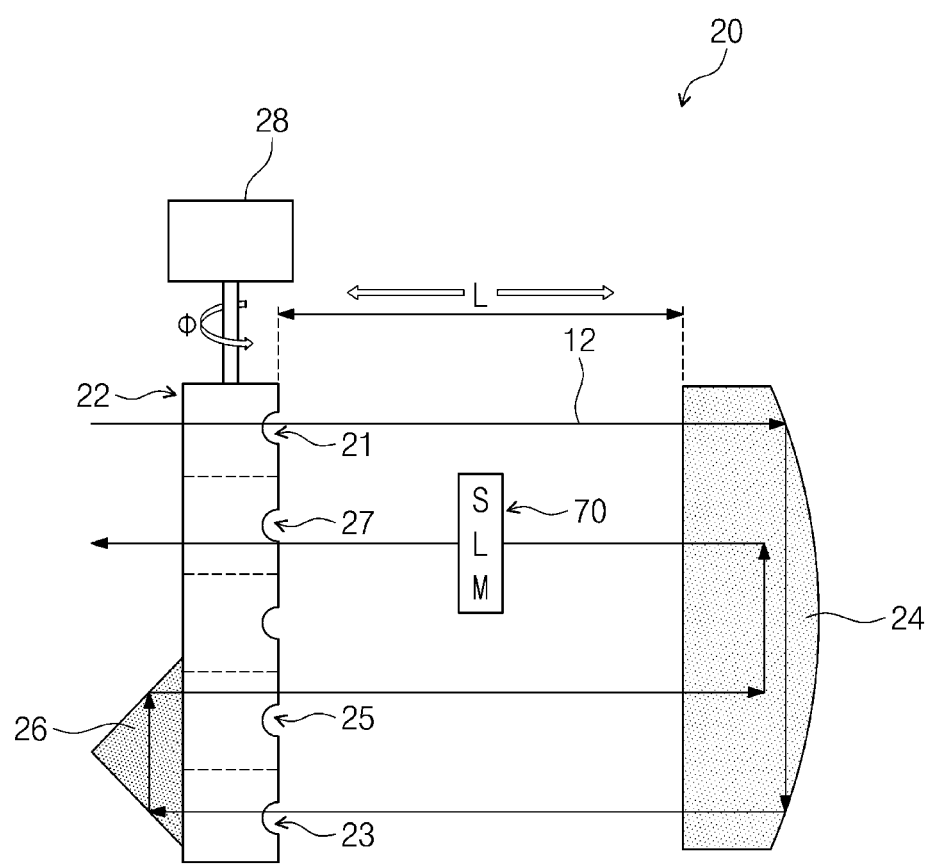
FIG. 5 is a cross-sectional view showing another example of a pulse compressor of FIG. 1.

FIG. 5 shows another example of the pulse compressor 20 of FIG. 1.

Referring to FIG. 5, the pulse compressor 20 may further include a spatial light modulator (SLM) 70. The SLM 70 may be provided between a grating plate 22 and a corner cube 24. For example, the SLM 70 may be adjacent to a fourth diffraction region 27 and provided within the path of the laser beam 12. On the other hand, the SLM 70 may be provided in the outside of the fourth diffraction region 27 at an output end of the pulse compressor 20, but the embodiment of the inventive concept is not limited thereto. The spectral phases of the output end of the pulse compressor 20, optical components constituting the two-photon excited fluorescence microscope 100, and the human eyeballs or the animal eyeballs are measured in advance. The SLM 70 is programmed to correct the measured spectral phases, and thus the dispersion value of the laser beam 12 may be reduced at higher order.

As described above, the two-photon excited fluorescence microscope according to an embodiment of the inventive concept may obtain the high-resolution images of fundus by using the pulse compressor which adjusts the dispersion value of the laser beam to the negative value, thereby diagnosing the Alzheimer's disease or the mild cognitive impairment (MCI) which is a previous stage of dementia. The pulse compressor may be reduced in size by using the corner cube and the retroreflector which are respectively disposed to both the sides of the grating plate to repeatedly reflect the laser beam to the grating plate, and may have the wavelength changing function.

The foregoing description is about detailed examples for practicing the inventive concept. The present disclosure includes not only the above-described embodiments but also simply changed or easily modified embodiments. In addition, the present disclosure may include techniques which may be easily modified and practiced by using the embodiments described above.

What is claimed is:

1. A two-photon excited fluorescence microscope comprising:
    a light source configured to generate a laser beam;
    a pulse compressor configured to compress a pulse of the laser beam;
    an objective lens configured to direct the laser beam to a specimen;
    image sensors configured to receive the laser beam and obtain surface and internal images of the specimen,
    wherein the pulse compressor comprises:
        a grating plate configured to disperse the laser beam;
        a corner cube provided on a first side of the grating plate and configured to reflect the laser beam to the grating plate; and
        a retroreflector provided on a second side of the grating plate and configured to re-reflect the laser beam, which has been transmitted through the grating plate, to the corner cube and the grating plate.

2. A two-photon excited fluorescence microscope comprising:
    a light source configured to generate a laser beam;
    a pulse compressor configured to compress a pulse of the laser beam;
    an objective lens configured to provide the laser beam to a specimen; and
    image sensors configured to receive the laser beam and obtain images of the specimen,
    wherein the pulse compressor comprises:
    a grating plate configured to disperse the laser beam;
    a corner cube provided on a first side of the grating plate and configured to reflect the laser beam to the grating plate; and
    a retroreflector provided on a second side of the grating plate and configured to re-reflect the laser beam, which has been transmitted through the grating plate, to the corner cube and the grating plate, and
    wherein the grating plate comprises:
        a first diffraction region;
        a second diffraction region spaced apart from the first diffraction region;
        a third diffraction region between the second diffraction region and the first diffraction region; and
        a fourth diffraction region between the third diffraction region and the first diffraction region.

3. The two-photon excited fluorescence microscope of claim 2,
    wherein the retroreflector is in contact with the second diffraction region and the third diffraction region, and
    wherein the retroreflector is spaced apart from the first diffraction region and the fourth diffraction region.

4. The two-photon excited fluorescence microscope of claim 2,
    wherein the pulse compressor further comprises a rotator, and
    wherein the rotator is connected to a side wall of the grating plate adjacent to the first diffraction region to rotate the grating plate.

5. The two-photon excited fluorescence microscope of claim 2,
    wherein the pulse compressor further comprises a cylinder, and
    wherein the cylinder is provided between the third diffraction region and the fourth diffraction region to adjust a distance between the grating plate and the corner cube.

6. The two-photon excited fluorescence microscope of claim 1, wherein the light source comprises a femtosecond pulse laser.

7. The two-photon excited fluorescence microscope of claim 1, further comprising beam splitters provided between the pulse compressor and the objective lens.

8. The two-photon excited fluorescence microscope of claim 7, wherein the beam splitters comprise:
    a first beam splitter; and
    a second beam splitter between the first beam splitter and the objective lens.

9. The two-photon excited fluorescence microscope of claim 8, further comprising tube lenses between the pulse compressor and the first beam splitter.

10. The two-photon excited fluorescence microscope of claim 9, further comprising planar mirrors between the tube lenses and the pulse compressor.

11. A pulse compressor comprising:
    a grating plate configured to disperse a laser beam;
    a corner cube provided on a first side of the grating plate and configured to reflect the laser beam to the grating plate;
    a retroreflector provided on a second side of the grating plate and configured to re-reflect the laser beam, which has been transmitted through the grating plate, to the corner cube and the grating plate; and
    a rotator connected to a side wall of the grating plate, the sidewall positioned between the first side of the grating plate and the second side of the grating plate,
    wherein the rotator is configured to rotate the grating plate to adjust a dispersion value of the laser beam.

12. The pulse compressor of claim 11, wherein the grating plate comprises:
    a first diffraction region adjacent to the rotator;
    a second diffraction region spaced apart from the first diffraction region;
    a third diffraction region between the second diffraction region and the first diffraction region; and
    a fourth diffraction region between the third diffraction region and the first diffraction region.

13. The pulse compressor of claim 12,
wherein the retroreflector is in contact with the second diffraction region and the third diffraction region, and
wherein the retroreflector is spaced apart from the first diffraction region and the fourth diffraction region.

14. The pulse compressor of claim 12, further comprising a cylinder provided between the third diffraction region and the fourth diffraction region,
wherein the cylinder is configured to adjust a distance between the grating plate and the corner cube.

15. The pulse compressor of claim 12, further comprising a spatial light modulator provided between the grating plate and the corner cube.

16. The pulse compressor of claim 15, wherein the spatial light modulator is provided adjacent to the fourth diffraction region.

\* \* \* \* \*